(12) United States Patent
Wang et al.

(10) Patent No.: US 11,100,635 B2
(45) Date of Patent: Aug. 24, 2021

(54) AUTOMATIC PAN-TILT-ZOOM ADJUSTMENT TO IMPROVE VITAL SIGN ACQUISITION

(71) Applicant: KONINKLIJKE PHILIPS N.V., Eindhoven (NL)

(72) Inventors: Haibo Wang, Melrose, MA (US); Cornelis Conradus Adrianus Maria van Zon, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 110 days.

(21) Appl. No.: 16/343,827

(22) PCT Filed: Oct. 31, 2017

(86) PCT No.: PCT/EP2017/077842
§ 371 (c)(1),
(2) Date: Apr. 22, 2019

(87) PCT Pub. No.: WO2018/083074
PCT Pub. Date: May 11, 2018

(65) Prior Publication Data
US 2019/0251689 A1   Aug. 15, 2019

Related U.S. Application Data

(60) Provisional application No. 62/416,781, filed on Nov. 3, 2016.

(51) Int. Cl.
*G06T 7/00* (2017.01)
*G16H 30/20* (2018.01)
(Continued)

(52) U.S. Cl.
CPC .............. *G06T 7/0012* (2013.01); *G06T 7/70* (2017.01); *G16H 30/20* (2018.01); *G16H 40/63* (2018.01);
(Continued)

(58) Field of Classification Search
CPC . G06T 2207/30004; G06T 2207/30196; G06T 7/0012; G06T 7/70; G16H 30/20;
(Continued)

(56) References Cited

U.S. PATENT DOCUMENTS 7,151,562 B1   12/2006   Trajkovic
8,059,154 B1   11/2011   Kiro et al.
(Continued)

OTHER PUBLICATIONS

Hague, M., "Visual analysis of faces with application in biometrics, forensics and health informatics", Aalborg University, Apr. 1, 2016, 340 pages (Abstract).
(Continued)

*Primary Examiner* — Manuchehr Rahmjoo

(57) ABSTRACT

Techniques disclosed herein relate to automatic pan-tilt-zoom adjustment to improve vital sign acquisition. In various embodiments, a vital sign acquisition camera (176) operable to pan, tilt, and zoom ("PTZ") may capture (402) an image of a patient (100). The image may be analyzed (404) to detect a depicted position of the patient within an image coordinate space of the image. A desired position of the patient within the image coordinate space of the image may determined (406), and a difference in the image coordinate space between the depicted position and the desired position may be calculated (408). The difference may then be mapped (410) from the image coordinate space to a PTZ space. One or more PTZ parameters of the vital sign acquisition camera may be altered (412) based on the mapping. After altering the one or more PTZ parameters, the
(Continued)

vital sign acquisition camera may acquire (414) one or more vital signs from the patient.

15 Claims, 7 Drawing Sheets

(51) Int. Cl.
    *G06T 7/70*     (2017.01)
    *G16H 40/63*     (2018.01)
    *H04N 5/232*     (2006.01)

(52) U.S. Cl.
    CPC ..... *H04N 5/23296* (2013.01); *H04N 5/23299* (2018.08); *G06T 2207/30004* (2013.01); *G06T 2207/30196* (2013.01)

(58) Field of Classification Search
    CPC . G16H 40/63; H04N 5/23296; H04N 5/23299
    See application file for complete search history.

(56) References Cited

U.S. PATENT DOCUMENTS

| | | |
|---|---|---|
| 8,819,788 B2 | 8/2014 | Shachar et al. |
| 2003/0052971 A1 | 3/2003 | Gutta et al. |
| 2008/0001735 A1* | 1/2008 | Tran .................. G06F 19/00 340/539.22 |
| 2011/0128385 A1 | 6/2011 | Bedros et al. |
| 2013/0169822 A1 | 7/2013 | Zhu et al. |
| 2014/0253711 A1 | 9/2014 | Balch et al. |

OTHER PUBLICATIONS

Chauvin, et al., "Contact-Free Respiration Rate Monitoring Using a Pan-Tilt Thermal Camera for Stationary Bike Telerehabilitation Sessions", IEEE Systems Journal, vol. 10, No. 3, Sep. 1, 2016, pp. 1046-1055.

Sankaranarayanan, et al., "PTZ Camera Modeling and Panoramic View Generation via Focal Plane Mapping", Asian Conference on Computer Vision, Nov. 2010, pp. 580-593.

Wu, et al., "Keeping a Pan-Tilt-Zoom Camera Calibrated", IEEE Transactions on Pattern Analysis and Machine Intelligence, vol. 35, No. 8, Aug. 2013, pp. 1994-2007.

International Search Report and Written Opinion for International Application Serial No. PCT/EP2017/077842, filed Oct. 31, 2017, 17 pages.

* cited by examiner

AUTOMATIC PAN-TILT-ZOOM ADJUSTMENT TO IMPROVE VITAL SIGN ACQUISITION

CROSS-REFERENCE TO PRIOR APPLICATIONS

This application is the U.S. National Phase application under 35 U.S.C. § 371 of International Application No. PCT/EP2017/077842, filed on Oct. 31, 2017, which claims the benefit of U.S. Provisional Application Ser. No. 62/416,781, filed Nov. 3, 2016. These applications are hereby incorporated by reference herein, for all purposes.

TECHNICAL FIELD

The present disclosure is directed generally to health care. More particularly, but not exclusively, various methods and apparatus disclosed herein relate to unobtrusively acquiring vital signs from patients.

BACKGROUND

There are a variety of scenarios in which it would be desirable to unobtrusively (e.g., without making contact) acquire vital signs from patients. For example, when patients visit the emergency department of a hospital, they typically are triaged to determine various information about the patients, such as their names, ages, heights, weights, vital signs, reasons for visiting, and other similar information. Once triaged, the patients are sent to an area such as a waiting room to wait for hospital resources such as physicians to become available to examine and/or treat the patients. Wait times for the patients may be significant depending on availability of hospital resources, and during these waits their conditions may deteriorate. Requiring busy hospital personnel to manually monitoring these patients' conditions for deterioration is often prohibitive. Similarly, the conditions of outpatients at home may deteriorate over time, and yet deploying hospital personnel to the outpatients' homes to monitor the outpatients may require inordinate resources.

SUMMARY

The present disclosure is directed to methods, systems, and apparatus for monitoring changes in conditions of patients using so-called "vital sign acquisition cameras" that are configured to unobtrusively acquire a variety of vital signs from patients without expending significant resources. These vital signs may include but are not limited to temperature, pulse rate, peripheral capillary oxygen saturation ("$SpO_2$"), respiration rate, posture, and so forth. In order for vital sign acquisition cameras to accurately and efficiently obtain vital signs from patients, it may be preferable that the patients be located at a particular position within a frame of the vital sign acquisition camera. Accordingly, techniques are described herein for automatically adjusting various parameters of vital sign acquisition cameras to ensure that patients are properly positioned within the frame. For example, in some embodiments, a vital sign acquisition camera may obtain the most accurate vital signs when it is properly aimed and/or focused on a patient's head and/or torso.

Generally, in one aspect, a method may include: capturing, by a vital sign acquisition camera, an image of a patient, wherein the vital sign acquisition camera is operable to pan, tilt, and zoom ("PTZ"); analyzing the image to detect a depicted position of the patient within an image coordinate space of the image; determining a desired position of the patient within the image coordinate space of the image; calculating a difference in the image coordinate space between the depicted position and the desired position; mapping the difference from the image coordinate space to a PTZ space; altering one or more PTZ parameters of the vital sign acquisition camera based on the mapping; and after altering the one or more PTZ parameters, acquiring, by the vital sign acquisition camera, one or more vital signs from the patient.

In various embodiments, the analyzing may include detecting one or more sizes of one or more depicted portions of the patient within the image coordinate space of the image. In various embodiments, the method may further include determining one or more desired sizes of the one or more depicted portions of the patient within the image coordinate space of the image. In various embodiments, the difference in the image coordinate space may include one or more scale differences between the detected one or more sizes of the one or more depicted portions of the patient and the one or more desired sizes. In various embodiments, the mapping may be based on prior calibration of the vital sign acquisition camera. In various embodiments, the prior calibration may include estimating a focal length at each of a plurality of zoom levels of the vital sign acquisition camera.

Other implementations may include a non-transitory computer readable storage medium storing instructions executable by a processor to perform a method such as one or more of the methods described above. Yet another implementation may include a control system including memory and one or more processors operable to execute instructions, stored in the memory, to implement one or more modules or engines that, alone or collectively, perform a method such as one or more of the methods described above.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosure.

DETAILED DESCRIPTION

There are a variety of scenarios in which it would be desirable to unobtrusively (e.g., without making contact) acquire vital signs from patients. For example, when patients visit the emergency department of a hospital, they typically are registered and triaged to determine various information about the patients, such as their names, ages, heights, weights, vital signs, reasons for visiting, and other similar information. At triage, their urgency to see a physician and an estimate of resources required for diagnosis and treatment are established. Once registered and triaged, the patients are sent to an area such as a waiting room to wait for hospital resources such as physicians to become available to examine and/or treat the patients. Wait times for the patients may be significant depending on availability of hospital resources, and during these waits their conditions may deteriorate. Requiring busy hospital personnel to manually monitor these patients' conditions for deterioration would be prohibitive. Similarly, the conditions of outpatients at home may deteriorate over time, and yet deploying hospital personnel to the outpatients' homes to monitor the outpatients may require inordinate resources.

Figure 1:
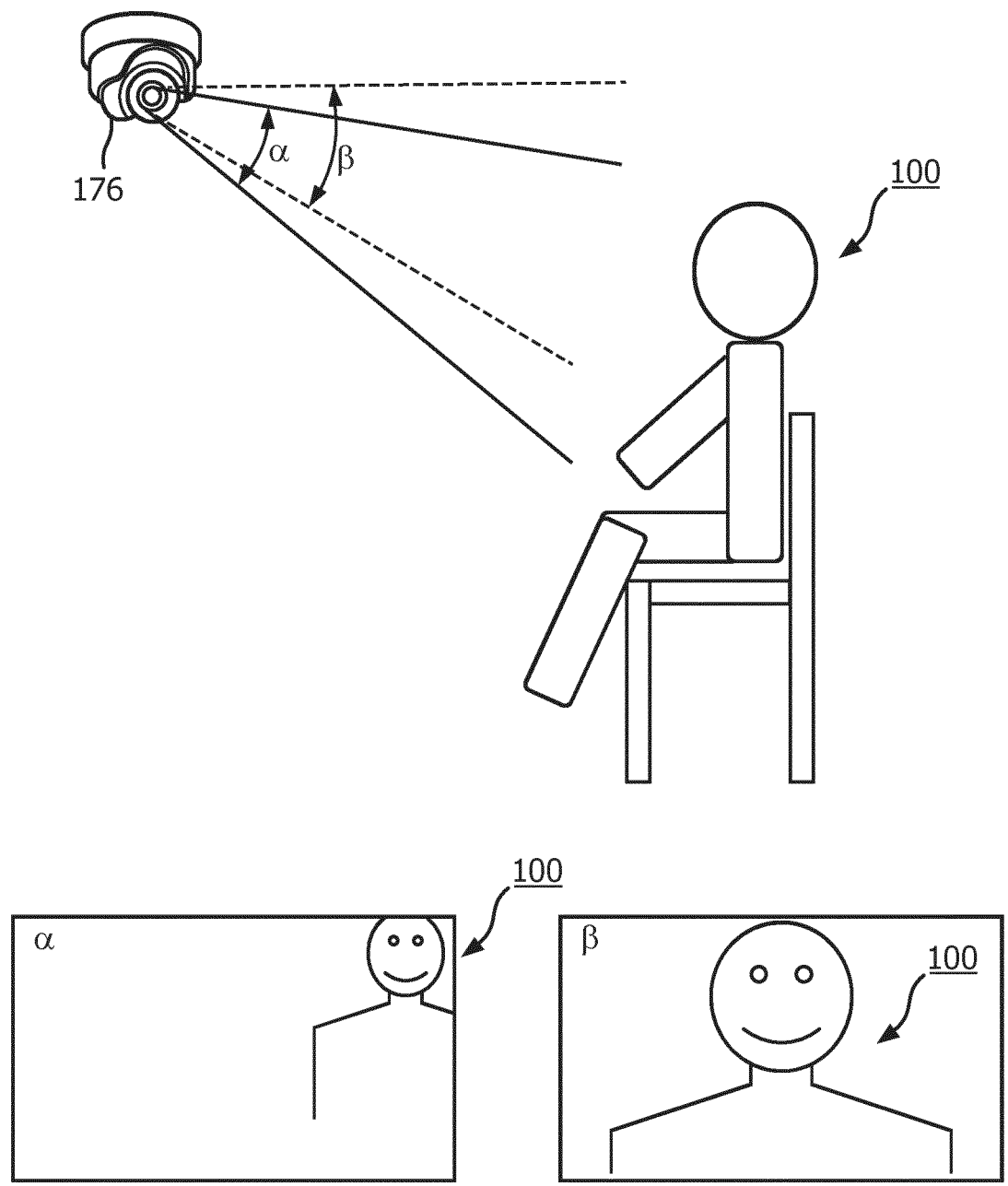
FIG. 1 schematically illustrates a scenario in which selected aspects of the present disclosure may be practiced, in accordance with various embodiments.
Figure 6:
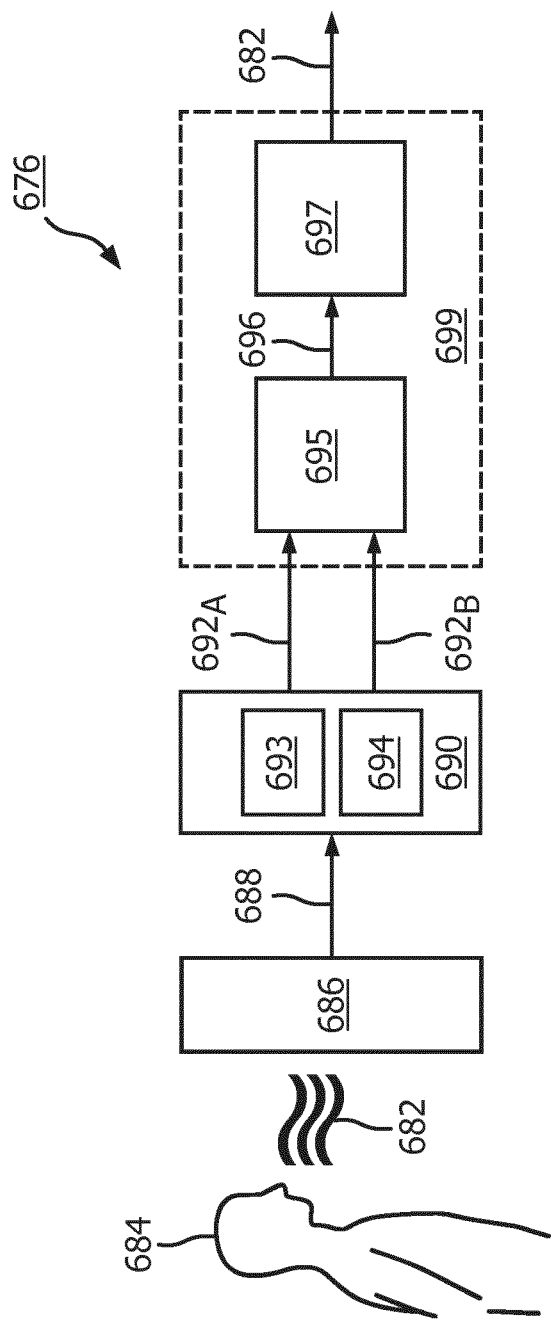
FIGS. 6 and 7 schematically depict non-limiting examples of components of two example vital sign acquisition cameras, in accordance with various embodiments.
Figure 7:
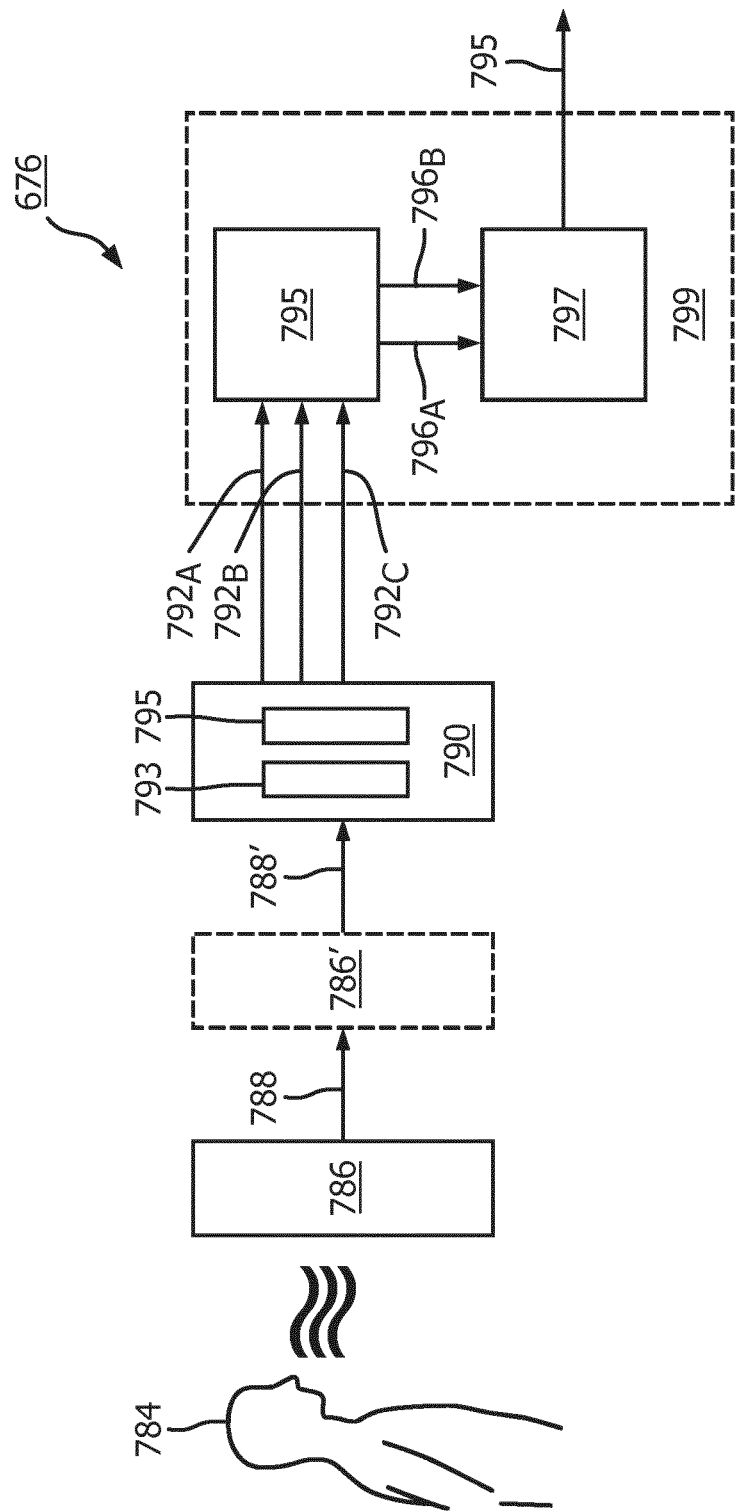

FIG. 1 schematically illustrates an example of how techniques described herein may be employed, in accordance with various embodiments. A patient 100 is seated in an area in which patient 100 is to be unobtrusively monitored by one or more vital sign acquisition cameras 176. In various embodiments, vital sign acquisition camera 176 may be a so-called "pan-tilt-zoom" ("PTZ") camera that is adjustable in the so-called "PTZ space" to point at different locations (e.g., by adjusting pan and tilt parameters) and to capture images at various zoom levels (e.g., by adjusting a zoom parameter). In various embodiments, vital sign acquisition camera 176 may be equipped to perform so-called "contactless methods" to acquire vital signs and other physiological information from patient 100. Non-limiting examples of such cameras are described in United States Patent Application Publication Nos. 20140192177A1, 20140139656A1, 20140148663A1, 20140253709A1, 20140235976A1, and 20140275880A1, which are incorporated herein by reference for all purposes. FIGS. 6 and 7 schematically depict two non-limiting configurations of vital sign acquisition cameras that may be employed in various embodiments of the present disclosure.

In FIG. 1, vital sign acquisition camera 176 is initially configured in the PTZ space to capture patient 100 in the angle α. It can be seen from the corresponding frame at bottom left that when so-adjusted, patient 100 is positioned off-center within the frame α (to the right and up). Moreover, patient 100 is relatively small within the frame α. In other words, patient 100 is sub-optimally framed. In such a PTZ configuration, vital sign acquisition camera 176 may not be able to accurately and/or efficiently capture one or more vital signs. For example, a torso of patient 100 may be too small within the frame to accurately capture respiration rate.

Accordingly, in various embodiments, vital sign acquisition camera 176 may be configured with selected aspects of the present disclosure to automatically reconfigure itself (or be reconfigured by another computing device, not depicted) in order to capture patient 100 within its frame in a more optimal manner. In particular, one or more PTZ parameters of vital sign acquisition camera 176 may be automatically adjusted based on a detected position of patient 100 within its frame to more optimally capture patient 100 for purposes of acquiring one or more vital signs.

In FIG. 1, one or more PTZ parameters of vital sign acquisition camera 176 may be automatically adjusted so that patient 100 is captured in the angle β, for which a corresponding frame β is depicted at bottom right. For example, the detected position of patient 100 within the frame α (i.e., within so-called "image coordinate space" of the frame, i.e., Cartesian space) may be compared to a desired position of patient 100 within the frame to determine a difference in scale and/or displacement of patient 100 between the detected and desired positions. This difference in image coordinate space may then be mapped to the PTZ space of vital sign acquisition camera 176. One or more PTZ parameters of vital sign acquisition camera 176 may be adjusted based on the mapping, and vital sign acquisition camera 176 may then be operated to acquire one or more vital signs from the patient. It can be seen in frame/that patient 100 is now more or less centered within the frame and occupies a larger portion of the frame. Consequently, vital sign acquisition camera 176 is able to unobtrusively capture vital sign(s) from patient 100 more accurately.

The mapping between image coordinate space and PTZ space may be determined in various ways, and may be specific to the particular vital sign acquisition camera 176 being used. Accordingly, in various embodiments, vital sign acquisition camera 176 may be calibrated (e.g., offline) to establish the mapping from image coordinate space to PTZ space. In some embodiments, calibration may include implementation of techniques such as those described in "PTZ Camera Modeling and Panoramic View Generation via Focal Plane Mapping," by Karthik Sankaranarayananan and James W. Davis, *Asian Conference on Computer Vision*, November 2010, which is incorporated herein by reference in its entirety for all purposes. That paper describes how the mapping may rely on the camera's focal length f, which differs at each optical zoom level Z. In some embodiments, a test subject may be positioned at a distance from vital sign acquisition camera 176. An optical zoom setting of vital sign acquisition camera 176 may be adjusted from low to high, e.g., from the range of zero to twenty in increments of one. At each optical zoom setting, a focal length f may be calculated. The focal length f may be calculated at each optical zoom setting in various ways.

Figure 2:
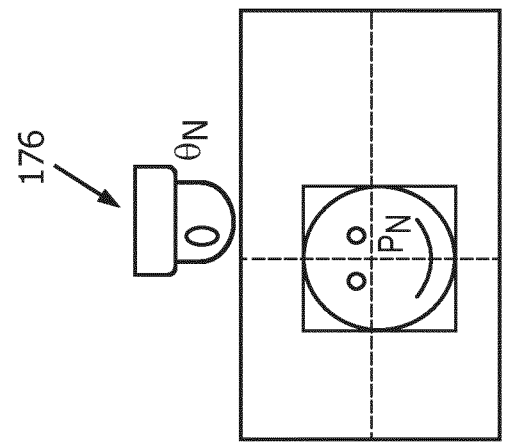
FIG. 2 illustrates one example of how a vital sign acquisition camera may be calibrated to generate a mapping between image coordinate space and pan-tilt-zoom space, in accordance with various embodiments.
Figure 2:
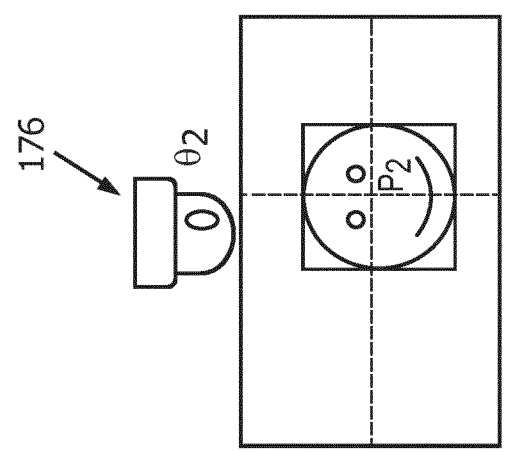
Figure 2:
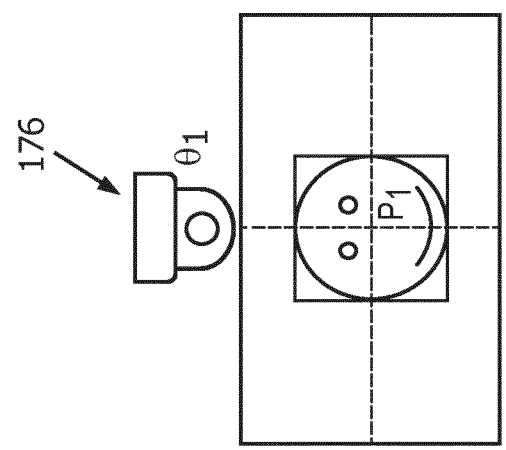

FIG. 2 demonstrates one non-limiting technique for calculating focal length f at each optical zoom setting z. For each optical zoom setting z a pan setting (or parameter) θ of vital sign acquisition camera 176 may be varied among a plurality N of arbitrarily selected values, $\{\theta_1, \theta_2, \theta_3, \ldots, \theta_N\}$. At each pan setting $\theta_i$, a reference point $P_i$ of the test subject, such as a center of the test subject's face, may be detected in image coordinate space (e.g., using facial detection processing on an image captured using vital sign acquisition camera 176). In this manner, a plurality N of reference points of the test subject, $\{P_1, P_2, P_3, \ldots, P_N\}$, may be generated. Each reference point P may include an x coordinate and a y coordinate in image coordinate space.

Then, for each pair of arbitrarily select pan settings, $\{\theta_i, \theta_j\}$, a focal length f can be calculated using equations such as the following:

$$\delta\theta = \tan^{-1}\left(\frac{x}{y\sin\phi + f\cos\phi}\right) \quad (1)$$

$$\delta\phi = \tan^{-1}\left(\frac{\frac{y+a}{\cos\left(\tan^{-1}\left(\frac{a}{b} \cdot \frac{x}{y+a}\right)\right)} - a}{f}\right) \quad (2)$$

$$\delta\theta_i + |\delta\theta_j| = \theta_j - \theta_i \quad (3)$$

$\delta\theta$ represents a change in pan $\theta$, between $\theta_j$ and $\delta\phi$ and do represents a change in tilt $\phi$ (which may be 0 if tilt is not altered). The parameters a and b may be camera-related parameters that can be determined using equations such as the following:

$$a = f/\tan{-}\phi$$

$$b = a/\sin\phi$$

Equation (1) may be plugged into equation (3). $\theta_i$, $\theta_j$, are known, which means the only unknown in the resulting equation is the focal length f. Accordingly, the resulting equation may be solved for f. Then, an average $f_{avg}$ of all calculated focal lengths f from all the N(N−1)/2 selected pan pairs at the current optical zoom level z may be calculated, and that average $f_{avg}$ may be used as the accepted focal length f for the current optical zoom level z of vital sign acquisition camera 176. Then, vital sign acquisition camera 176 may be adjusted to the next optical zoom setting z and the process may be repeated.

Other similar techniques may be employed to calibrate vital sign acquisition camera 176 to establish the mapping between image coordinate space and PTZ space. For example, some cameras may include a plurality of discrete zoom settings s, e.g., 1-20, that a user may select to achieve a desired zoom level. Each discrete zoom setting s of the camera may be associated with a particular optical zoom level z that is implemented when the user selects the discrete zoom setting s. For at least some cameras, the relationship between discrete zoom levels s of the camera and corresponding implemented optical zoom levels z may be available, e.g., as part of a user manual. When optical zoom levels z are available in this way, a focal length f at least optical zoom level may be directly estimated, e.g., using an equation such as the following $$f = z*C$$

wherein C is a constant greater than zero that may estimated from the configuration of the PTZ camera being used and which may be camera-dependent.

Figure 3:
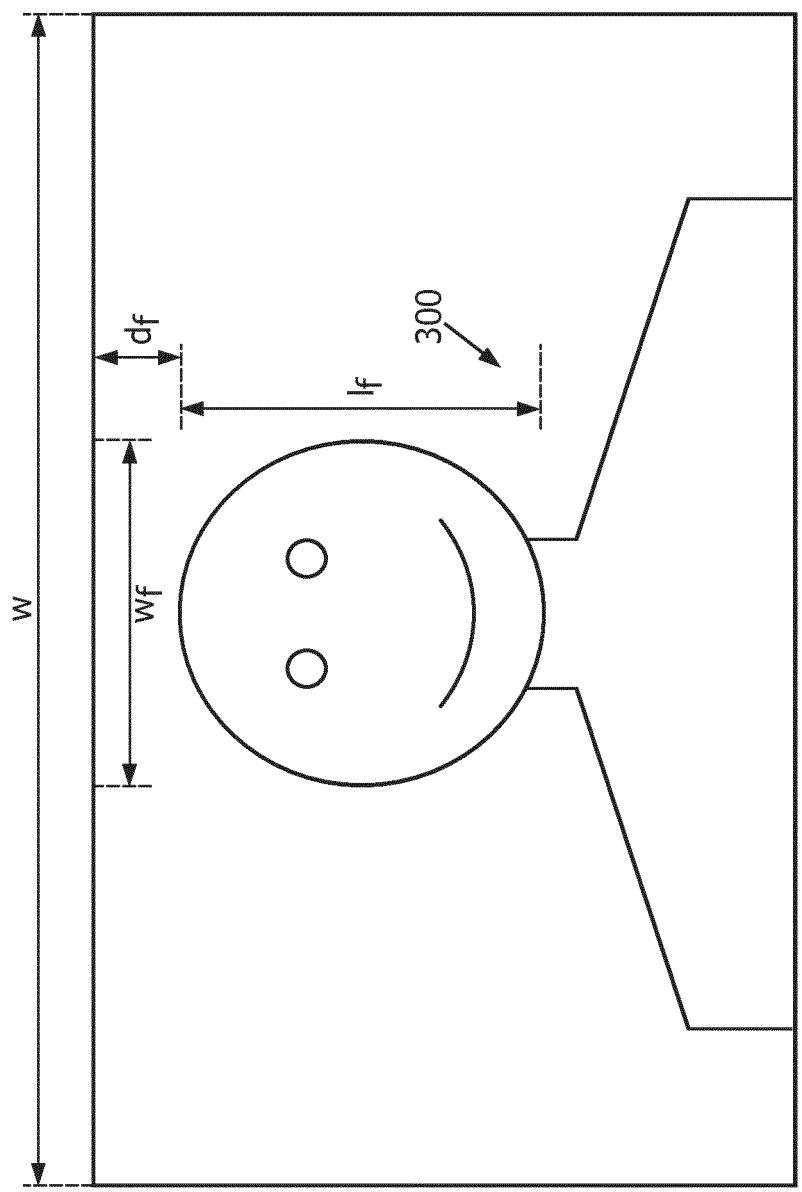
FIG. 3 depicts an example of a desired patient position within a frame of a vital sign acquisition camera, in accordance with various embodiments.

Once the mapping between image coordinate space and PTZ is established, e.g., using one of the techniques set forth above, vital sign acquisition camera 176 may be reconfigured (i.e. its PTZ parameters may be adjusted) automatically whenever a patient-to-be-monitored is captured within its frame, so that the patient can be properly positioned within the frame for improved vital sign acquisition. As noted above, in some embodiments, a depicted position of a patient within a frame may be compared with a "desired" position of the patient within the frame. The desired position of the patient in the frame may be determined in various ways. In some embodiments, the desired position may be an empirically-determined "ideal" position that may include one or more defined points of the patient's face and/or torso being at various locations and/or having various scales/sizes in the image coordinate space. For example, and as is depicted in FIG. 3, in some embodiments, the following values may be used for desired face position as an offset from the top of the frame, $d_f$, and desired face width, $w_f$:

$$d_f = 0.1 l_f$$

$$w_f = 0.33 w$$

$$z_f = w_f * z_d / w_d$$

$$l_f = z_f * l_d / z_d$$

wherein $l_f$ equals the length of the patient's face top-to-bottom (e.g., in pixels), w is the width of the frame (e.g., in pixels), and $w_d$, $l_d$ and $z_d$ are the detected face width, length and scale, respectively. However, this is just one example, and any other values may be used instead.

Once the difference (e.g., displacement and/or change in scale) is determined between the detected position of patient 100 within the frame and the desired position, Equations (1)-(3) described above may be used to determine the mapping to PTZ space. With this mapping, the PTZ parameters of image acquisition camera may be adjusted, so that vital signs may be acquired from patient 100.

Figure 4:
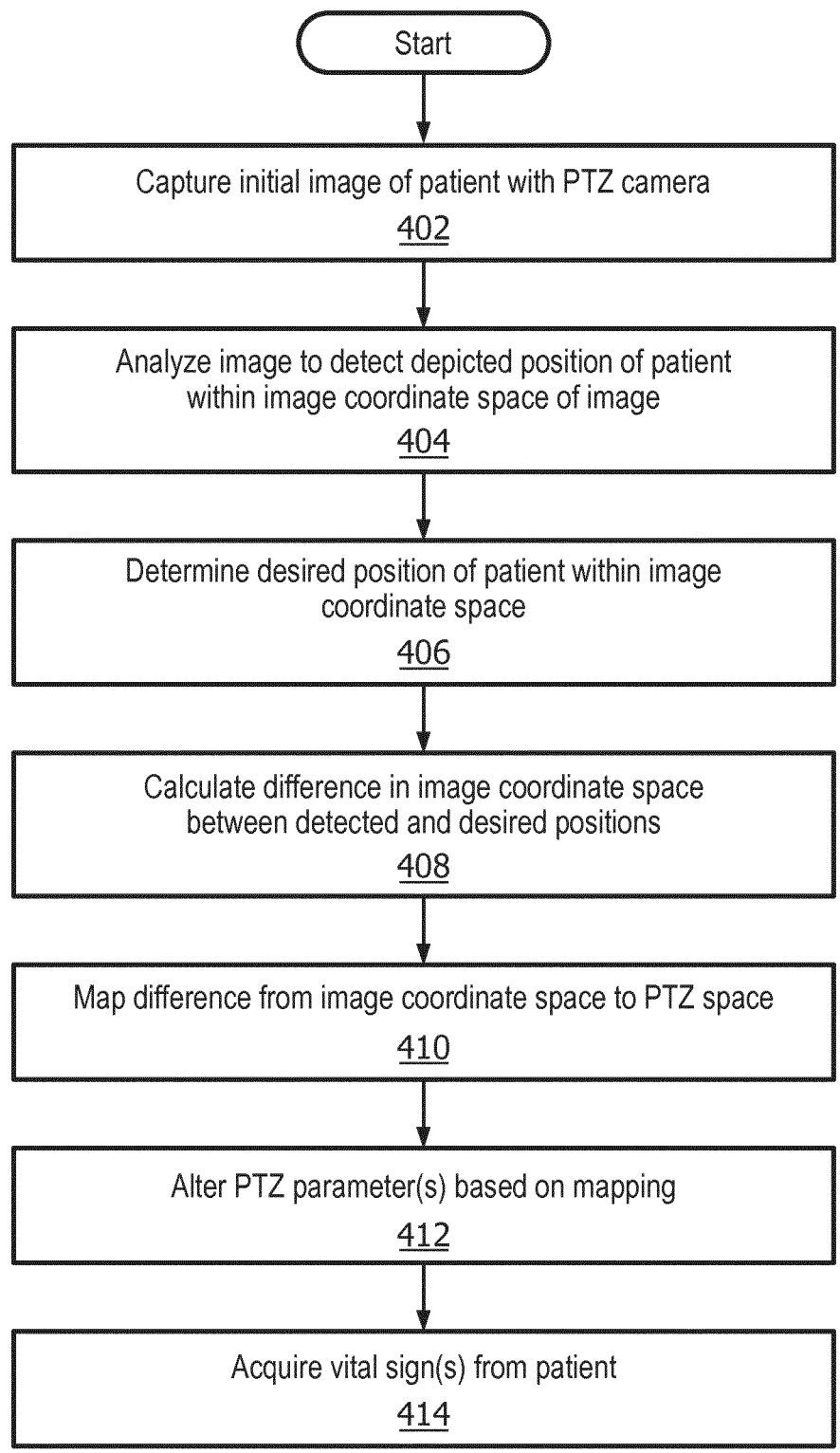
FIG. 4 depicts an example method for practicing various aspects of the present disclosure, in accordance with various embodiments.

FIG. 4 depicts an example method 400 for automatically adjusting one or more PTZ parameters of a vital sign acquisition camera (e.g., 100) so that vital signs may be unobtrusively acquired from a patient. For convenience, some of the operations of method 400 are described with reference to a system that performs the operations. This system may include various components of various computer systems, including internal logic (e.g., FPGA, ASIC, microprocessor) of vital sign acquisition camera 176 itself. Moreover, while operations of method 400 are shown in a particular order, this is not meant to be limiting. One or more operations may be reordered, omitted or added.

At block 402, the system may capture an initial image of a patient-to-be-monitored with a PTZ camera, such as the vital sign acquisition camera 176 described above. For example, vital sign acquisition camera 176 may scan an area such as a waiting room filled with patients or an outpatient's home and capture an image when it detects a patient within its frame. In some embodiments, vital sign acquisition camera 176 may scan an area using a predetermined trajectory, such as a trajectory that passes one or more rows of chairs in which waiting patients may be sitting, or a trajectory that iterates through locations in an outpatient's home that are known to be inhabited frequently by the outpatient.

However the initial image of the patient is captured, at block 404, the system may analyze the image to detect a depicted position of the patient within the coordinate space (e.g., x, y space) of the image. The system may detect the patient's depicted position in various ways. In some embodiments, the system may employ techniques such as edge detection to detect outer edges of the patient within the image frame. In other embodiments, the system may perform face detection to detect the patient's depicted face position within the image frame. The depicted position of the patient's face within the frame may include a variety of information, such as the patient's absolute position, sizes of one or more portions of the patient (e.g., head, neck, shoulders, etc.), relative positions of one or more portions of the patient, and so forth. Some of the spatial metrics that may be detected were described above with respect to FIG. 3.

At block 404, the system may determine a desired position of the patient within the coordinate space of the image. In some embodiments, a desired position of the patient may be preset manually to include one or more constants, e.g., such as $d_f$ and $l_f$ described above with respect to FIG. 3. In some embodiments, the desired position of the patient may be determined and/or dynamically adjusted based on a variety of factors, such as lighting within the room, clothing worn by the patient (which may affect how respiration rate may be detected from the patient's torso), a size of the patient, a health condition of the patient, and so forth.

Referring back to FIG. 4, however the desired position of the patient within the frame is determined, at block 408, a difference between the detected position of patient determined at block 404 and the desired position determined at block 406 in image coordinate space may be calculated. In various embodiments, this difference may include translational components (e.g., translation along the x and y axes) and/or scaling components (e.g., the patient's head needs to be enlarged by a factor of $\delta z$.

At block 410, the system may map the difference in image coordinate space calculated at block 408 to PTZ space of vital sign acquisition camera 176. As described above, this mapping may be based on the calibration of vital sign acquisition camera 176 where a focal length f at each zoom level z was calculated. In some embodiments, equations such as Equation (1)-(3) above may be used to map the difference in image coordinate space to PTZ space of vital sign acquisition camera 176. In various embodiments, the mapping may include a change in pan ($\delta\theta$), a change in tilt ($\delta\phi$), and/or a change in zoom ($\delta z$).

At block 412, the system may alter one or more PTZ parameters of vital sign acquisition camera 176 based on the mapping (e.g., $\delta\theta$, $\delta\phi$, $\delta z$) of block 410. At block 414, the system may operate vital sign acquisition camera 176 to unobtrusively acquire one or more vital signs from the patient. As noted above, these vital signs may include but are not limited to temperature, pulse rate, peripheral capillary oxygen saturation ("$SpO_2$"), respiration rate, posture, and so forth.

Figure 5:
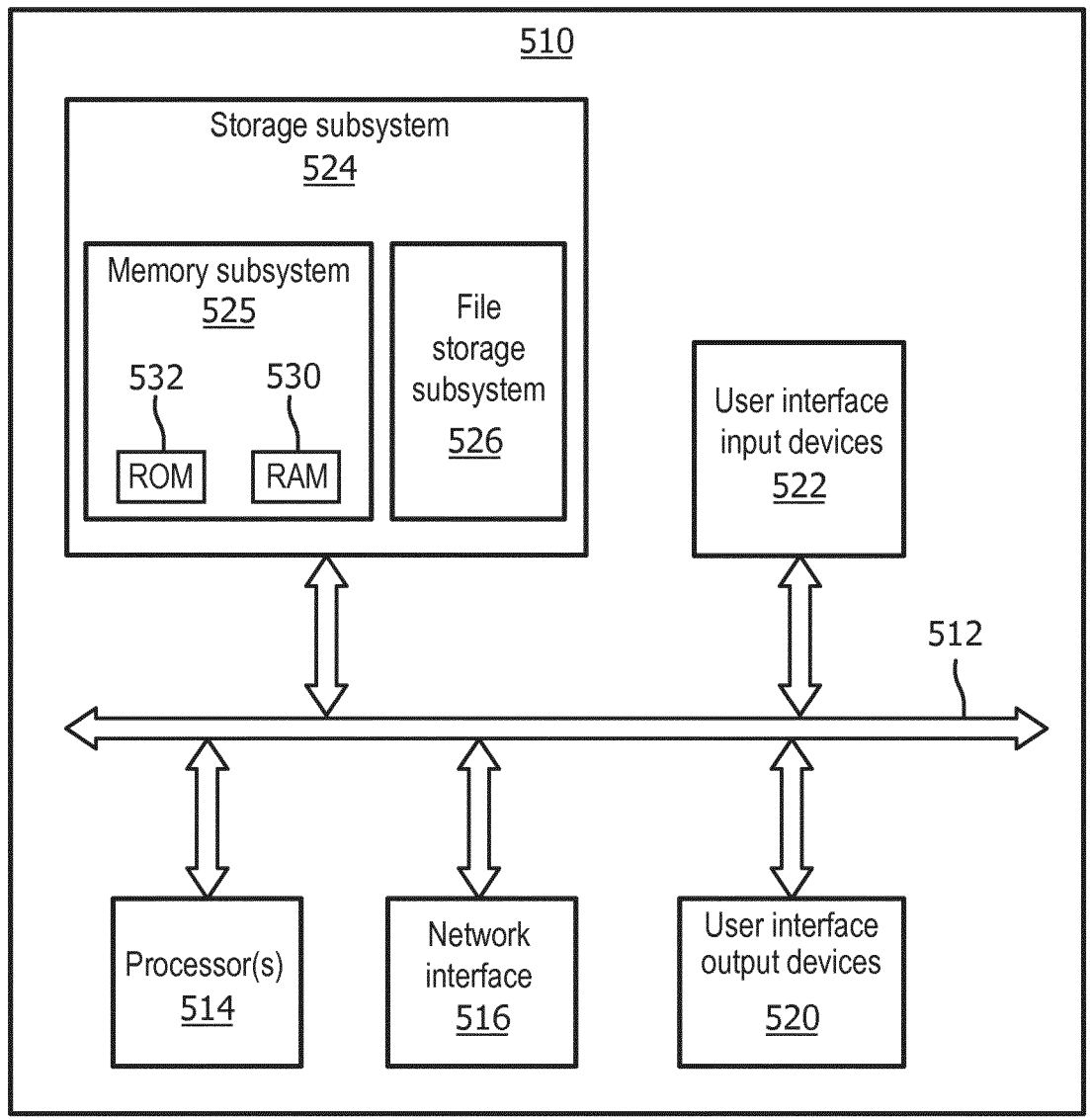
FIG. 5 depicts components of an example computer system.

FIG. 5 is a block diagram of an example computer system 510. Computer system 510 typically includes at least one processor 514 which communicates with a number of peripheral devices via bus subsystem 512. As used herein, the term "processor" will be understood to encompass various devices capable of performing the various functionalities attributed to the CDS system described herein such as, for example, microprocessors, FPGAs, ASICs, other similar devices, and combinations thereof. These peripheral devices may include a data retention subsystem 524, including, for example, a memory subsystem 525 and a file storage subsystem 526, user interface output devices 520, user interface input devices 522, and a network interface subsystem 516. The input and output devices allow user interaction with computer system 510. Network interface subsystem 516 provides an interface to outside networks and is coupled to corresponding interface devices in other computer systems.

User interface input devices 522 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 510 or onto a communication network.

User interface output devices 520 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 510 to the user or to another machine or computer system.

Data retention system 524 stores programming and data constructs that provide the functionality of some or all of the modules described herein. For example, the data retention system 524 may include the logic to perform selected aspects of method 400, and/or to implement one or more components of vital sign acquisition camera 176 or a computing device that controls operation of vital sign acquisition camera 176.

These software modules are generally executed by processor 514 alone or in combination with other processors. Memory 525 used in the storage subsystem can include a number of memories including a main random access memory (RAM) 530 for storage of instructions and data during program execution, a read only memory (ROM) 532 in which fixed instructions are stored, and other types of memories such as instruction/data caches (which may additionally or alternatively be integral with at least one processor 514). A file storage subsystem 526 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 526 in the data retention system 524, or in other machines accessible by the processor(s) 514. As used herein, the term "non-transitory computer-readable medium" will be understood to encompass both volatile memory (e.g. DRAM and SRAM) and non-volatile memory (e.g. flash memory, magnetic storage, and optical storage) but to exclude transitory signals.

Bus subsystem 512 provides a mechanism for letting the various components and subsystems of computer system 510 communicate with each other as intended. Although bus subsystem 512 is shown schematically as a single bus, alternative implementations of the bus subsystem may use multiple busses.

Computer system 510 can be of varying types including a workstation, server, computing cluster, blade server, server farm, or any other data processing system or computing device. In some embodiments, computer system 510 may be implemented within a cloud computing environment. Due to the ever-changing nature of computers and networks, the description of computer system 510 depicted in FIG. 4 is intended only as a specific example for purposes of illustrating some implementations. Many other configurations of computer system 510 are possible having more or fewer components than the computer system depicted in FIG. 5.

FIG. 6 shows a schematic diagram of a first embodiment of a vital sign acquisition camera 676 that may be employed in various embodiments described herein. Electromagnetic radiation 682, in particular light in the visible and infrared wavelength range, reflected from a living being 684, such as a patient, is received and evaluated by said camera 676 to generate a biometrical signal 698 of the living being 684. The camera 676 may include a filter 686 for blocking incident visible light within the incident electromagnetic radiation 682 in a wavelength range up to substantially 550 nm, and/or up to approximately 600 nm, and/or up to 650 nm. The filtered incident light 688 is then sensed by a color sensor 690 that generates at least two different color signals $692_A$, $692_B$, e.g. by use of two separate color detectors 693, 694 (or an array of such color detectors). A combination unit 695 generates at least one combined color signal 696 by combining said color signals $692_A$, $692_B$, e.g. by a linear combination. Finally, a processing unit 697 is provided for processing said combined color signal 696 and extracting at least one biometrical signal 698 of the living being 684. The combination unit 695 and the processing unit 697 may be realized in some embodiments by a common processor 699, e.g. as processing elements of a processor or implemented in software on a conventional processor. However, they may also be realized in a different manner, e.g. as dedicated hardware elements.

FIG. 7 schematically shows a second embodiment of a camera 776' that may be employed in various embodiments described herein. FIG. 7 shows that optionally an additional filter 786' may be provided (in this and/or other embodiments), which filter 786' is configured to block incident light in a wavelength range above at least 1100 nm, in particular above at least 1000 nm, before reaching the color sensor 790. While generally those color sensors, e.g. imaging silicon sensors, show a sensitivity that naturally decreases towards longer wavelengths, such an additional filter 786' may ensure that signal contributions within the filtered incident light 788 above said upper threshold wavelength are blocked, i.e. signal contributions in which water absorption becomes dominant are blocked in the twice filtered incident light 788'.

Further, in this embodiment the color sensor 790 generates three different color signals $792_A$, $792_B$, $792_C$, e.g. by use of a color filter array 793 having three different color filter areas provided in front of a photo detector 795 (or, more generally, the image sensor). Such a color sensor (e.g. including a color filter array having only two color filter areas) could also be used in the embodiment shown in FIG. 6. In some embodiments, the color sensor 790 may include a color filter array generating a red color signal $792_A$, a green color signal $792_B$ and a blue color signal $792_C$ as conventionally provided by an RGB color sensor. From the three color signals $792_A$, $792_B$, $792_C$, the combination unit 795 generates two combined color signals $796_A$, $796_B$ by making two different combinations, in particular linear combinations, of at least two of said three color signals $792_A$, $792_B$, $792_C$. From these two combined color signals $796_A$, $796_B$ the processing unit then finally extracts the desired biometrical signal 798 from the living being 784.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope

What is claimed is:

1. A computer-implemented method, comprising:
   capturing, by a vital sign acquisition camera, an image of a patient, wherein the vital sign acquisition camera is operable to pan, tilt, and zoom ("PTZ");
   analyzing the image to detect a depicted position and size of the patient within an image coordinate space of the image, a detected width of the patient's face within the imagine coordinate space of the image, and a detected length of the patient's face within the image coordinate space of the image;
   determining a desired position and size of the patient within the image coordinate space of the image, determining the desired position and size including:
      determining a desired width of the patient's face within the image coordinate space of the image as a first predetermined percentage of a width of the image coordinate space of the image, wherein the first predetermined percentage is not 100 percent;
      determining a desired zoom scale as the desired width of the patient's face within the image coordinate space of the image times a detected zoom scale of the image of the patient divided by the detected width of the patient's face within the image coordinate space of the image;
      determining a desired length of the patient's face within the image coordinate space of the image as the desired zoom scale times the detected length of the patient's face within the image coordinate space of the image divided by the detected zoom scale of the image of the patient; and
      determining a desired offset of the patient's face from a top of the image coordinate space of the image as a second predetermined percentage of the desired length of the patient's face within the image coordinate space of the image, wherein the second predetermined percentage is not 0 percent,
   wherein the desired position and size of the patient within the image coordinate space of the image is based on the desired width of the patient's face, the desired length of the patient's face, and the desired offset of the patient's face from the top of the image coordinate space of the image;
   calculating a difference in the image coordinate space between the depicted position and size and the desired position and size;
   mapping the difference from the image coordinate space to a PTZ space;
   altering one or more PTZ parameters of the vital sign acquisition camera based on the mapping; and
   after altering the one or more PTZ parameters, acquiring, by the vital sign acquisition camera, one or more vital signs from the patient.

2. The computer-implemented method of claim 1, wherein the analyzing includes detecting one or more sizes of one or more depicted portions of the patient within the image coordinate space of the image.

3. The computer-implemented method of claim 2, further comprising:
   determining one or more desired sizes of the one or more depicted portions of the patient within the image coordinate space of the image;
   wherein the difference in the image coordinate space includes one or more scale differences between the detected one or more sizes of the one or more depicted portions of the patient and the one or more desired sizes.

4. The computer-implemented method of claim 1, wherein the mapping is based on prior calibration of the vital sign acquisition camera.

5. The computer-implemented method of claim 4, wherein the prior calibration includes estimating a focal length at each of a plurality of zoom levels of the vital sign acquisition camera.

6. A system comprising one or more processors and memory operably coupled with the one or more processors, wherein the memory stores instructions that, in response to execution of the instructions by one or more processors, cause the one or more processors to:
   capture, by a vital sign acquisition camera, an image of a patient, wherein the vital sign acquisition camera is operable to pan, tilt, and zoom ("PTZ");
   analyze the image to detect a depicted position and size of the patient within an image coordinate space of the image, a detected width of the patient's face within the image coordinate space of the image, and a detected length of the patient's face within the image coordinate space of the image;
   determine a desired width of the patient's face within the image coordinate space of the image as a first predetermined percentage of a width of the image coordinate space of the image, wherein the first predetermined percentage is not 100 percent;
   determine a desired zoom scale as the desired width of the patient's face within the image coordinate space of the image times a detected zoom scale of the image of the patient divided by the detected width of the patient's face within the image coordinate space of the image;
   determine a desired length of the patient's face within the image coordinate space of the image as the desired zoom scale times the detected length of the patient's face within the image coordinate space of the image divided by the detected zoom scale of the image of the patient; and
   determine a desired offset of the patient's face from a top of the image coordinate space of the image as a second predetermined percentage of the desired length of the patient's face within the image coordinate space of the image, wherein the second predetermined percentage is not 0 percent,
wherein the desired position and size of the patient within the image coordinate space of the image is based on the desired width of the patient's face, the desired length of the patient's face, and the desired offset of the patient's face from the top of the image coordinate space of the image;
calculate a difference in the image coordinate space between the depicted position and size and the desired position and size;
map the difference from the image coordinate space to a PTZ space;
alter one or more PTZ parameters of the vital sign acquisition camera based on the mapping; and
after altering the one or more PTZ parameters, acquire, by the vital sign acquisition camera, one or more vital signs from the patient.

7. The system of claim 6, further comprising instructions to detect one or more sizes of one or more depicted portions of the patient within the image coordinate space of the image.

8. The system of claim 7, further comprising instructions to:
determine one or more desired sizes of the one or more depicted portions of the patient within the image coordinate space of the image;
wherein the difference in the image coordinate space includes one or more scale differences between the detected one or more sizes of the one or more depicted portions of the patient and the one or more desired sizes.

9. The system of claim 6, wherein the mapping is based on prior calibration of the vital sign acquisition camera.

10. The system of claim 9, wherein the prior calibration includes estimating a focal length at each of a plurality of zoom levels of the vital sign acquisition camera.

11. At least one non-transitory computer-readable medium comprising instructions that, in response to execution of the instructions by one or more processors, cause the one or more processors to perform the following operations
capturing, by a vital sign acquisition camera, an image of a patient, wherein the vital sign acquisition camera is operable to pan, tilt, and zoom ("PTZ");
analyzing the image to detect a depicted position and size of the patient within an image coordinate space of the image, a detected width of the patient's face within the image coordinate space of the image, and detected length of the patient's face within the image coordinate space of the image;
determining a desired position and size of the patient within the image coordinate space of the image, determining the desired position and size including:
determining a desired width of the patient's face within the image coordinate space of the image as a first predetermined percentage of a width of the image coordinate space of the image, wherein the first predetermined percentage is not 100 percent;
determine a desired zoom scale as the desired width of the patient's face within the image coordinate space of the image times a detected zoom scale of the image of the patient divided by the detected width of the patient's face within the image coordinate space of the image;
determine a desired length of the patient's face within the image coordinate space of the image as the desired zoom scale times the detected length of the patient's face within the image coordinate space of the image divided by the detected zoom scale of the image of the patient; and
determine a desired offset of the patient's face from a top of the image coordinate space of the image as a second predetermined percentage of the desired length of the patient's face within the image coordinate space of the image, wherein the second predetermined percentage is not 0 percent,
wherein the desired position and size of the patient within the image coordinate space of the image is based on the desired width of the patient's face, the desired length of the patient's face, and the desired offset of the patient's face from the top of the image coordinate space of the image;
calculating a difference in the image coordinate space between the depicted position and size and the desired position and size;
mapping the difference from the image coordinate space to a PTZ space;
altering one or more PTZ parameters of the vital sign acquisition camera based on the mapping; and
after altering the one or more PTZ parameters, acquiring, by the vital sign acquisition camera, one or more vital signs from the patient.

12. The at least one non-transitory computer-readable medium of claim 11, wherein the analyzing includes detecting one or more sizes of one or more depicted portions of the patient within the image coordinate space of the image.

13. The at least one non-transitory computer-readable medium of claim 12, further comprising instructions that cause the one or more processors to perform the following operations:
determining one or more desired sizes of the one or more depicted portions of the patient within the image coordinate space of the image;
wherein the difference in the image coordinate space includes one or more scale differences between the detected one or more sizes of the one or more depicted portions of the patient and the one or more desired sizes.

14. The at least one non-transitory computer-readable medium of claim 11, wherein the mapping is based on prior calibration of the vital sign acquisition camera.

15. The at least one non-transitory computer-readable medium of claim 14, wherein the prior calibration includes estimating a focal length at each of a plurality of zoom levels of the vital sign acquisition camera.

* * * * *